United States Patent [19]

Ramachandran

[11] Patent Number: 4,482,502

[45] Date of Patent: Nov. 13, 1984

[54] PREPARATION OF BIARYL COMPOUNDS

[75] Inventor: Venkataraman Ramachandran, Baton Rouge, La.

[73] Assignee: Ethyl Corporation, Richmond, Va.

[21] Appl. No.: 488,192

[22] Filed: Apr. 25, 1983

[51] Int. Cl.$^3$ .................. C07C 121/66; C07C 69/616
[52] U.S. Cl. ................................. 260/465 G; 546/330; 546/342; 549/74; 549/79; 560/100; 560/102; 562/492
[58] Field of Search ................... 260/465 G; 560/102; 562/492

[56] References Cited

U.S. PATENT DOCUMENTS 3,992,459  11/1976  Utne et al. ..................... 260/649 F
4,370,278   1/1983  Stahly et al. .................... 260/465 E

FOREIGN PATENT DOCUMENTS 57-16830  1/1982  Japan .
2065655   7/1981  United Kingdom .

Primary Examiner—Dolph H. Torrence
Attorney, Agent, or Firm—Donald L. Johnson; John F. Sieberth; Patricia J. Hogan

[57] ABSTRACT

Biaryl compounds are prepared by coupling an arylamine with an aromatic compound in the presence of an alkyl nitrite and about 0.04–0.6 mol of an acid having a dissociation constant of at least about $1.7 \times 10^{-5}$ at 25° C. and about 0.08–1.3 mols of a cuprous halide catalyst per mol of the arylamine. The invention has particular utility in the coupling with aromatic compounds of arylamines having acid-sensitive ar-substituents, e.g. flurbiprofen intermediates, such as 2-(4-amino-3-fluorobenzene)propionitrile and alkyl 2-(4-amino-3-fluorobenzene)propionates.

29 Claims, No Drawings

PREPARATION OF BIARYL COMPOUNDS

Technical Field

This invention relates to biaryl compounds and more particularly relates to an aryl coupling process for preparing them.

Background

As disclosed in U.S. Pat. No. 3,992,459 (Utne et al.), in U.K. Patent Application No. 2 065 655 A (Upjohn), and in Japanese Kokai Patent Application SHO No. 57[1982]-16830 (Sagami), it is known that biphenyl compounds can be prepared by reacting an aniline with an second aryl component in the presence of an alkyl nitrite, an acid, and a copper catalyst. Utne et al. teach that the amount of acid employed in their alkyl nitrite reaction should be in the range of 1.1–1.5 mols per mol of the aniline compound; and their example illustrating this embodiment of their invention, i.e., Example 5, discloses the use of about 1.5 mols of acid per mol of aniline compound. The broad teachings of Upjohn and Sagami do not specify the amounts of acid that should be employed in their alkyl nitrate processes; but their relevant examples show the use of about 1.5–2.3 mols of acid per mol of aniline compound and suggest that an increase in the amount of acid leads to an increase in the yield of product.

Although each of the aforementioned references broadly teaches the applicability of its processes to the coupling of a variety of aniline compounds with other aryl compounds, each limits its working examples to processes wherein the aniline is a dihalonaniline or carbalkoxyhaloaniline, and neither suggests how its teachings could be modified to permit an efficient coupling with aromatic compounds of arylamines outside the scope of its working examples. The use of arylamines different from those employed in the working examples of Utne et al., Upjohn, and Sagami, e.g., arylamines bearing acetonitrile or other substituents sensitive to copper/acid catalysts, hereinafter designated as acid-sensitive substituents, leads to much lower yields of biaryl compounds than are obtained by Utne et al., Upjohn, and Sagami, e.g., yields of about 3–30%; and it would obviously be desirable to find both a way of improving the yields of biaryls obtainable by coupling such arylamines with aromatic compounds and a way of improving such yields without increasing the amount of acid required in the catalyst composition.

Summary of Invention

An object of this invention is to provide a novel aryl coupling process.

Another object is to provide such a process which permits to production of a high yield of biaryl compound from an arylamine bearing an acid-sensitive substituent.

These and other objects are attained by using a critical amount of a particular copper/acid catalyst in a pseudo-Gomberg process for coupling an arylamine with an aromatic compound. Specifically, in a process for coupling an arylamine with an aromatic compound in the presence of an alkyl nitrite, a copper catalyst, and an acid, the invention resides in the improvement of employing about 0.04–0.6 mol of an acid having a dissociation constant of at lease about $1.7 \times 10^{-5}$ at 25° C. and about 0.08–1.3 mols of a cuprous halide catalyst per mol of the arylamine.

Detailed Description

Arylamines utilizable in the practice of the invention can be any arylamines capable of being coupled with other aromatic compounds via diazo intermediates. However, the particular utility of the invention resides in the treatment of arylamines which normally lead to poor yields of biaryl compounds when subjected to pseudo-Gomberg reactions utilizing copper/acid catalyst, i.e., arylamines bearing one or more acid-sensitive ar-substituents acid-sensitive substituents being those, such as cyanoalkyl, carboxyalkyl, alkylcarbalkoxy, etc., which have a tendency to be detrimentally affected by the use of copper/acid catalysts. Such compounds may be derivatives of carbocyclic aromatic compounds, such as benzene, naphthalene, etc., or heterocyclic aromatic compounds, such as pyridine, thiophene, etc.; and they may bear no substituents other than the amino and acid-sensitive substituents, or they may bear one or more other substituents, such as alkyl, alkoxy, alkoxycarbonyl, cycloalkyl, phenyl, phenoxy, nitro, halo, cyano, etc.

A preferred embodiment of the invention is its application to the coupling of arylamines which are aminohalobenzenes bearing one or more acid-sensitive substituents. Such compounds are anilines having at least one halo substituent and at least one acid-sensitive substituent on the aromatic ring. The halo substituents may be bromo, chloro, iodo, or fluoro; and the acid-sensitive substituents may be any group corresponding to the formula:

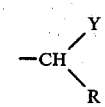

wherein R is hydrogen or an alkyl group, generally an alkyl group of 1–6 carbons; and Y is an acid-sensitive group, such as —CN, —COOR', etc.—R' being aryl, cycloalkyl, alkyl (generally an alkyl group of 1–6 carbons), etc. Exemplary of such compounds are aminohalobenzeneacetonitriles, such as 2-(aminofluorobenzene)propionitriles, and alkyl aminohalobenzeneacetic acid esters, such as alkyl 2-(aminofluorobenzene)propionates. Particularly preferred aminohalobenzenes are 2-(4-amino-3-fluorobenzene)propionitrile and alkyl 2-(4-amino-3-fluorobenzene)propionates, which are ideally suited for the preparation of flurbiprofen intermediates by the process of the invention.

Aromatic compounds which can be coupled with arylamines in the process of the invention are substituted and unsubstituted carbocyclic and heterocyclic compounds such as benzene, naphthalene, pyridine, thiophene, etc.—any substituents generally being substituents such as hydroxy, halo, nitro, alkyl, alkoxy, alkoxycarbonyl, aryloxycarbonyl, phenyl, cyano, or cycloalkyl, and any organic substituents generally containing not more than about 10, preferably not more than 4, carbons. The preferred aromatic compounds are benzene compounds, most preferably benzene itself. Since this component of the reaction mixture functions as a solvent as well as a reactant, and the amount used may affect the yield of product obtainable, it is employed in excess of the amount required to couple with the arylamine. Generally, the amount of aromatic compound employed is in the range of about 10-300, preferably about 50-150, mols per mol of arylamine.

The alkyl nitrite used to diazotize the arylamine may be any of the alkyl nitrites commonly employed in pseudo-Gomberg reactions, generally an alkyl nitrite containing 1-6 carbons, such as the n-butyl, isobutyl, t-butyl, isoamyl, and isopropyl, etc. nitrites. The amount of alkyl nitrite that should be employed varies with the degree of dilution of the reaction mixture and with the temperature used—larger amounts generally being required when the reaction mixture is more dilute and/or an elevated diazotization temperature is utilized. As a rule, the amount of alkyl nitrite employed is in the range of about 1-5 mols, preferably about 1-2 mols, per mol of arylamine.

Acids useful in the practice of the invention are relatively strong acids, i.e., acids having dissociation constants of at least about $1.7 \times 10^{-5}$, preferably at least about $1.0 \times 10^{-1}$ at 25° C. Such acids include inorganic acids, such as sulfuric, hydrochloric, etc., and organic acids, such as benzoic, chloroacetic, dichloroacetic, trichloroacetic, methanesulfonic, acetic, etc. In a preferred embodiment of the invention, the acid is trichloroacetic acid. The acid is employed in an amount such as to provide about 0.04-0.6, preferably about 0.2-0.4, mol per mol of arylamine.

The cuprous halide catalyst of the invention may be any cuprous halide, e.g., cuprous chloride, cuprous bromide, etc., which may be initially employed as the halide or a progenitor thereof. In one of the preferred embodiments of the invention, powdered copper is employed as a progenitor of the cuprous halide catalyst and allowed to react with the acid, prior to use in the reaction, to form the catalyst. This component of the reaction mixture is employed in an amount such as to provide about 0.08-1.3, preferably about 0.4-0.9, mols per mol of arylamine.

In addition to the aforementioned ingredients, the reaction mixture may contain optional ingredients, such as finelydivided inert solids capable of absorbing water, e.g., anhydrous magnesium sulfate, silica gel, diatomaceous earth, etc.

Except for the inventive modifications described above, the process of the invention may be conducted under any of the conditions normally employed for pseudo-Gomberg reactions. However, it is generally preferred to employ temperatures of about 0°-15° C., preferably about 5°-10° C., until the arylamine has been substantially completely diazotized and then raise the temperature to, e.g., room or reflux temperatures.

The following examples are given to illustrate the invention and are not intended as a limitation thereof.

EXAMPLE I

A catalyst slurry was prepared by mixing 0.7 molar proportion of copper powder with 0.3 molar proportion of trichloroacetic acid and 3.9 molar proportions of benzene under nitrogen and stirring the mixture for about 18 hours. Subsequently 90.5 molar proportions of benzene were added to the catalyst slurry, followed by 1.5 molar proportions of magnesium sulfate. After this mixture had been stirred for 30 minutes, a solution of a crude mixture containing one molar proportion of 2-(4-amino-3-fluorobenzene)propionitrile (AFPN) in 2 molar proportions of benzene was slowly dripped into the mixture over a period of 5 minutes. Next the addition funnel was flushed with an additional 2 molar proportions of benzene. The reaction mixture was then cooled to 10°-15° C., and 1.2 molar proportions of isopropyl nitrate were slowly added thereto over a period of 10 minutes to diazotize the AFPN. After diazotization was complete, the solution was warmed to room temperature over a period of four hours and worked up to isolate the product. The reaction resulted in a 95% yield of 2-(2-fluoro-4-biphenyl)propionitrile (FBPN).

EXAMPLE II

A catalyst slurry was prepared by mixing 0.9 molar proportion of copper powder with 0.3 molar proportion of trichloroacetic acid and 3.9 molar proportions of benzene, stirring the mixture overnight, adding 90.5 molar proportions of benzene and 1.5 molar proportions of magnesium sulfate to the stirred mixture, and continuing to stir the mixture until 48 hours after the beginning of the catalyst preparation. Then a solution of a crude mixture containing one proportion of AFPN in 2 molar proportions of benzene was dripped into the catalyst slurry over a period of 15 minutes, and an additional 2 molar proportions of benzene were added as a flush of the addition funnel. The reaction mixture was cooled to 10°-15° C., and 1.2 molar proportions of isopropyl nitrite were added dropwise over a period of 10 minutes to diazotize the AFPN. After diazotization was complete, the solution was warmed to room temperature over a period of 4 hours and worked up to isolate the product. The reaction resulted in an 88% yield of FBPN.

EXAMPLE III

Using the same general procedure as in the preceding examples, AFPN was reacted with isopropyl nitrite and benzene in several additional runs utilizing a catalyst slurry prepared by reacting copper powder with trichloroacetic acid in a portion of the benzene. As in the preceding examples, the reactions were conducted in the presence of 1.5 molar proportions of magnesium sulfate and utilized 1.2 molar proportions of isopropyl nitrite. The molar proportions of copper, acid, and benzene employed per molar proportion of AFPN, as well as the yield of FBPN obtained, are shown in Table I.

TABLE I

| Run | Molar Proportions | | | FBPN Yield (%) |
| --- | --- | --- | --- | --- |
| | Cu | Acid | Benzene | |
| 1 | 0.9 | 0.3 | 100 | 84 |
| 2 | 0.9 | 0.3 | 100 | 85 |
| 3 | 0.9 | 0.3 | 100 | 88 |
| 4 | 0.9 | 0.3 | 100 | 88 |
| 5 | 1.3 | 0.6 | 100 | 89 |
| 6 | 0.6 | 0.3 | 98 | 89 |
| 7 | 0.6 | 0.3 | 98 | 87 |
| 8 | 0.6 | 0.3 | 98 | 67 |
| 9 | 0.6 | 0.3 | 49 | 84 |
| 10 | 0.6 | 0.3 | 98 | 88 |

EXAMPLE IV

Using the same general procedure as in the proceding examples, three experiments were run in which one molar proportion of AFPN was reacted with 1.2 molar proportions of isopropyl nitrite and a total of 98 molar proportions of benzene in the presence of 1.5 molar proportions of magnesium sulfate and in the presence of a catalyst slurry obtained by mixing 0.5 molar proportion of cuprous chloride with, respectively, 0.04, 0.08, and 0.12 molar proportion of trichloroacetic acid and with a portion of the benzene. The reactions resulted in, respectively, 81%, 74%, and 82% yields of FBPN.

EXAMPLE V

A catalyst slurry was prepared by mixing 0.5 molar proportion of copper powder with 0.3 molar proportion of trichloroacetic acid and 50 molar proportions of benzene under nitrogen and stirring the mixture for 120–150 minutes. During this period, the copper slowly dissolved, initially causing the solution to turn green and then resulting in the formation of a bluish-gray precipitate. Subsequentially an additional 50 molar proportions of benzene were added, the reaction mixture was cooled to 5°–10° C., and the reaction vessel was subsequentially charged with one molar proportion of AFPN, 0.05–0.1 molar proportion of methanesulfonic acid, and 1.5 molar proportions of isopropyl nitrite. After diazotization was complete, in about 90–120 minutes, the reaction mixture was brought to room temperature, stirred for another 1–2 hours, and then worked up to isolate the product. The reaction resulted in a 94% yield of FBPN.

EXAMPLE VI

Three experiments were run by repeating Example V. One reaction resulted in an 82% yield of FBPN, and another in an 87% yield of FBPN. The other, in which no bluish-gray precipitate was formed during the catalyst preparation, resulted in a product that was unsuitable for analysis. It is believed that the problem associated with the last of these reactions—indicated by the absence of the usual precipitate—was caused by the absence of a reaction between the copper powder and the acid to form a cuprous halide catalyst.

EXAMPLE VII

Four experiments were run by repeating Example V except for employing only 1.1 molar proportions of isopropyl nitrite, conducting the diazotization at room temperature for about 10–15 minutes, and employing the benzene/AFPN molar ratios shown in Table II. The FBPN yields obtianed are also shown in Table II.

TABLE II

| Run | Benzene/AFPN Mol Ratio | FBPN Yield (%) |
|---|---|---|
| 11 | 100 | 88 |
| 12 | 50 | 82 |
| 13 | 20 | 59 |
| 14 | 100 | 87 |

EXAMPLE VIII

Four experiments were conducted by repeating Example V except for employing no methanesulfonic acid, adding the isopropyl nitrite to the reaction mixture prior to the AFPN, and varying the total amount of benzene as shown in Table III. The yields of FBPN obtained are also shown in Table III.

TABLE III

| Run | Benzene/AFPN Molar Ratio | FBPN Yield (%) |
|---|---|---|
| 15 | 100 | 88 |
| 16 | 100 | 89 |
| 17 | 50 | 84 |
| 18 | 25 | 76 |

EXAMPLE IX

A catalyst solution was prepared by mixing 0.4 molar proportion of copper powder with 0.3 molar proportion of trichloroacetic acid and 3.7 molar proportions of benzene, stirring the mixture under nitrogen for 40 minutes, diluting it with another 36.6 molar proportions of benzene, and continuing to stir. After 15 minutes, 0.04 molar proportion of methanesulfonic acid and 47.6 molar proportions of benzene were added, followed by one molar proportion of ethyl 2-(4-amino-3-fluorobenzene)propionate. Then 1.3 molar proportions of isopropyl nitrite and 7.3 molar proportions of benzene were added through an addition funnel over a period of 10 minutes so as to maintain the temperature at 20°–25° C. with the aid of a small amount of ice. Stirring was continued for another 15 minutes, after which the reaction mixture was worked up to isolate the product. The reaction resulted in a 75% yield of ethyl 2-(2-fluoro-4-biphenyl)propionate.

It is obvious that many variations may be made in the products and processes set forth above without departing from the spirit and scope of this invention.

I claim:

1. In a process for coupling an arylamine with an aromatic compound in the presence of an alkyl nitrite, a copper catalyst, and an acid, the improvement which comprises employing about 0.04–0.6 mol of an acid having a dissociation constant of at least about $1.7 \times 10^{-5}$ at 25° C. and about 0.08–1.3 mols of a cuprous halide catalyst per mol of the arylamine.

2. The process of claim 1 wherein the arylamine is an arylamine bearing an acid-sensitive ar-substituent.

3. The process of claim 2 wherein the acid-sensitive substituent is a cyanoalkyl group.

4. The process of claim 2 wherein the acid-sensitive substituent is an alkylcarbalkoxy group.

5. The process of claim 2 wherein the arylamine is an aminohalobenzeneacetonitrile.

6. The process of claim 5 wherein the aminohalobenezeneacetonitrile is a 2-(aminofluorobenzene)propionitrile.

7. The process of claim 6 wherein the 2-(aminoflourobenzene)propionitrile is 2-(4-amino-3-fluorobenzene)propionitrile.

8. The process of claim 2 wherein the arylamine is an alkyl aminohalobenzeneacetic acid ester.

9. The process of claim 8 wherein the alkyl aminohalobenzeneacetic acid ester is an alkyl 2-(aminofluorobenzene)propionate.

10. The process of claim 9 wherein the alkyl 2-(aminofluorobenzene)propionate is an alkyl 2-(4-amino-3-fluorobenzene)propionate.

11. The process of claim 1 wherein the aromatic compound is a benzene compound.

12. The process of claim 11 wherein the benzene compound is benzene.

13. The process of claim 1 wherein the alkyl nitrite is an alkyl nitrite containing 1–6 carbons.

14. The process of claim 13 wherein the alkyl nitrite is isopropyl nitrite.

15. The process of claim 1 wherein the acid is an acid having a dissociation constant of at least about $1.0 \times 10^{-1}$ at 25° C.

16. The process of claim 15 wherein the acid is trichloroacetic acid.

17. The process of claim 1 wherein the cuprous halide catalyst is cuprous chloride.

18. The process of claim 1 wherein the acid is trichloraocetic acid, the cuprous halide catalyst is cuprous chloride, and the cuprous chloride is formed by contacting powdered copper with the acid.

19. The process of claim 1 utilizing about 10–300 mols of the aromatic compound and about 1–5 mols of the alkyl nitrite per mol of the arylamine.

20. In a process for coupling 2-(4-amino-3-fluorobenzene)propionitrile with benzene in the presence of an alkyl nitrite to form 2-(2-fluoro-4-biphenyl)propionitrile via a diazo intermediate, the improvement which comprises conducting the reaction in the presence of aboout 0.04–0.6 mol of an acid having a dissociation constant of at least about $1.0 \times 10^{-1}$ at 25° C. and about 0.08–1.3 mols of a cuprous halide catalyst per mol of the 2-(4amino-3-fluorobenzene)propionitrile.

21. The process of claim 20 wherein the acid is trichloroacetic acid and the cuprous halide is cuprous chloride.

22. The process of claim 21 wherein the cuprous chloride is formed by contacting powdered copper with the acid.

23. The process of claim 22 wherein one molar proportion of 2-(4-amino-3-fluorobenzene)propionitrile is coupled with 50–150 molar proportions of benzene in the presence of 1–2 molar proportions of an alkyl nitrite and the total reaction product of about 0.2–0.4 molar proportion of trichloroacetic acid and about 0.4–0.9 molar proportion of powdered copper.

24. The process of claim 23 wherein the reaction is conducted at a temperature of about 5°–10° C. until diazotization of the 2-(4-amino-3-fluorobenzene) propionitrile is substantially complete.

25. In a process for coupling an alkyl 2-(4-amino-3-fluorobenzene)propionate with benzene in the presence of an alkyl nitrite to form an alkyl 2-(2-fluoro-4-biphenyl)propionate via a diazo intermediate, the improvement which comprises conducting the reaction in the presence of about 0.04–0.6 mol of an acid having a dissociation constant of at least about $1.0 \times 10^{-1}$ at 25° C. and about 0.08–1.3 mols of a cuprous halide catalyst per mol of the alkyl 2-(4-amino-3-fluorobenzene)propionate.

26. The process of claim 25 wherein the acid is trichloroacetic acid and the cuprous halide is cuprous chloride.

27. The process of claim 26 whrein the cuprous chloride is formed by contacting powdered copper with the acid.

28. The process of claim 27 wherein one molar proportion of an alkyl 2-(4-amino-3-fluorobenzene)propionate is coupled with 50–150 molar proportions of benzene in the presence of 1–2 molar proportions of an alkyl nitrite and the total reaction product of about 0.2–0.4 molar proportion of trichloroacetic acid and about 0.4–0.9 molar proportion of powdered copper.

29. The process of claim 28 wherein the reaction is conducted at a temperature of about 5°–10° C. until diazotization of the alkyl 2-(4-amino-3-fluorobenzene)propionate is substantially complete.

* * * * *